United States Patent
Chen

(10) Patent No.: US 10,058,690 B2
(45) Date of Patent: Aug. 28, 2018

(54) FACIAL MASK TRAY

(71) Applicant: I Ming Chen, Taipei (TW)

(72) Inventor: I Ming Chen, Taipei (TW)

( * ) Notice: Subject to any disclaimer, the term of this patent is extended or adjusted under 35 U.S.C. 154(b) by 0 days.

(21) Appl. No.: 15/447,367

(22) Filed: Mar. 2, 2017

(65) Prior Publication Data

US 2017/0259052 A1 Sep. 14, 2017

(30) Foreign Application Priority Data

Mar. 11, 2016 (TW) .................. 105203447

(51) Int. Cl.
*A61M 35/00* (2006.01)
*A45D 44/00* (2006.01)
*B65D 77/00* (2006.01)

(52) U.S. Cl.
CPC ........... *A61M 35/00* (2013.01); *A45D 44/002* (2013.01); *B65D 77/003* (2013.01); *A61M 2209/06* (2013.01)

(58) Field of Classification Search
CPC ........ A45D 33/18; A45D 33/24; A45D 33/26; A45D 40/30; A45D 44/00; A45D 44/002; A45D 44/22; A61M 35/00; A61M 2209/06; B65D 69/00; B65D 77/00; B65D 77/003
USPC .......................... 206/581, 823; 132/294–320
See application file for complete search history.

(56) References Cited

U.S. PATENT DOCUMENTS

| | | | |
|---|---|---|---|
| 6,631,806 B2* | 10/2003 | Jackson | A45D 40/22 206/457 |
| 7,165,559 B1* | 1/2007 | Goodman | A45D 33/18 132/294 |
| 7,631,766 B2* | 12/2009 | Wang | B65D 81/3272 206/222 |
| 2005/0217688 A1* | 10/2005 | Liu | A45D 40/30 132/216 |
| 2014/0298826 A1* | 10/2014 | Guor | A45D 44/002 206/581 |

* cited by examiner

*Primary Examiner* — Bryon Gehman
(74) *Attorney, Agent, or Firm* — Rosenberg, Klein & Lee

(57) ABSTRACT

A facial mask tray includes a plate-shaped plastic base. An accommodating socket is formed on the base for holding essences. The accommodating socket includes compaaments positionally corresponding to sites of a user's face that need focused skincare treatments. When filled with different essences according to the user's skincare needs, the compartments limit the essences in local sites on the base, so as to prevent the essences from diffusing inside the base and permeating to the whole base. When a substrate of a facial mask is placed into the accommodating socket, the substrate absorbs the essences in the compartments at its different parts locally, so that when put on a user's face, the facial mask provides focused skincare treatments specific to different facial skin parts, thereby improving the overall skincare effects.

5 Claims, 4 Drawing Sheets

FACIAL MASK TRAY

BACKGROUND OF THE INVENTION

1. Technical Field

The present invention relates to a facial mask tray for preparing and storing a facial mask. The tray has a base provided with an accommodating socket that includes one or more compartments in which one or more essences with skincare effects are filled. When placed into the accommodating socket, a substrate of a facial mask absorbs these essences at its different parts from the compartments so as to form a facial mask that provides a user's face with site-specific skincare effects.

2. Description of Related Art

For maintaining attractive appearance and deferring aging, many modern people take facial skincare as their important daily work. To cater for their needs, there are various products for facial skincare in the market, such as essences, facial masks, cream, and so on. Therein, facial masks are especially popular because they are affordable, easy to use, and effective.

For providing skincare that meets different user needs about skin treatment, manufacturers infuse facial masks with liquid ingredients that whiten, firm, or moisten skin according to the intended users' skin conditions. Such a facial mask is moist. In use, a user can directly put it on his/her face, and wait for the skincare ingredients of the facial mask to permeate into the user's face skin gradually, thereby achieving the intended skincare purposes.

However, different skin parts in one face can have different conditions and need diverse skincare treatments. For example, the cheeks and the eye lids tend to be dry, and the forehead has more sebum secretion, while the nose usually has more acnes. Thus, when a user uses a single facial mask for full-face treatment, the mask cannot provide site-specific focused care, and this significantly limits skincare effects of facial masks.

Hence, how to eliminate the defects and inconvenience as mentioned previously is an issue for relevant dealers to work on.

In view of the shortcomings of the prior art, the inventor of the present invention uses years of experience in the related fields and conducted repeated trials and modifications to finally invent a facial mask tray as disclosed herein.

SUMMARY OF THE INVENTION

The primary objective of the present invention is to provide a facial mask tray that has a base provided with an accommodating socket containing at least one compartment for receiving one or more essences so as to provide focused treatment specific to local skin conditions of different parts of a face to be cared. The compartments retain the essences at specific local sites on the base and prevent the essences from diffusing across the entire base. When a substrate of a facial mask is placed into the accommodating socket, the substrate absorbs the essences in the compartments at corresponding sites, so that one said facial mask when put on a user's face can provide local treatments specific to different conditions of facial skin parts, thereby improving the overall skincare effects.

The secondary objective of the present invention is to provide a facial mask tray that has a base provided with a plurality of cavities. When different essences are dilled into the accommodating socket of the base and at least one compartment, and a substrate of a facial mask is placed in the accommodating socket, minute gaps exist between the base and the facial mask due to spaces defined by the cavities. Capillarity thus exists between these gaps and the essences and holds the essences in the cavities, thereby preventing the essences from spilling out the base during transportation while providing users with improved skincare effects.

DETAILED DESCRIPTION OF THE INVENTION

Figure 1:
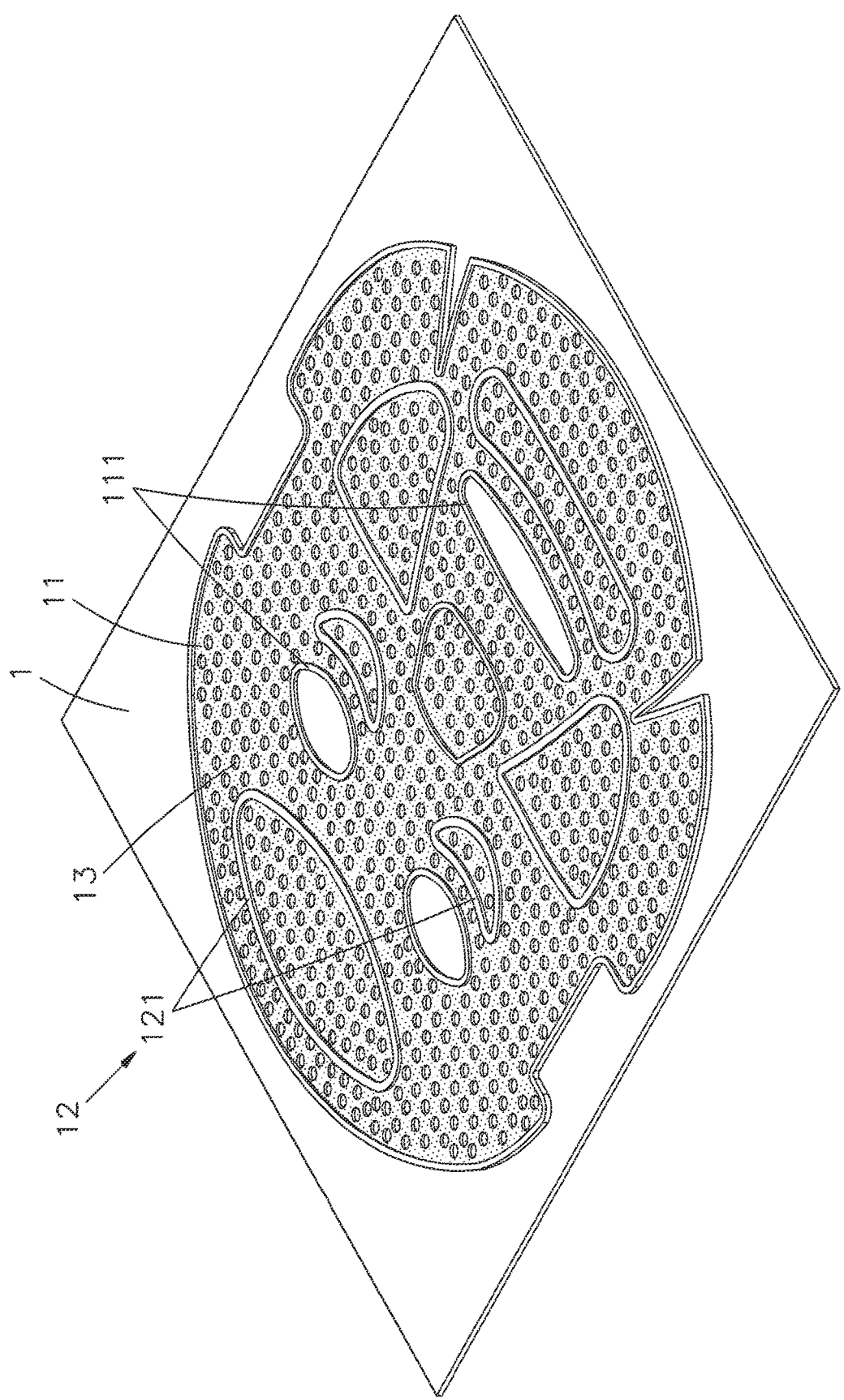
FIG. 1 is a perspective view of the present invention.
Figure 2:
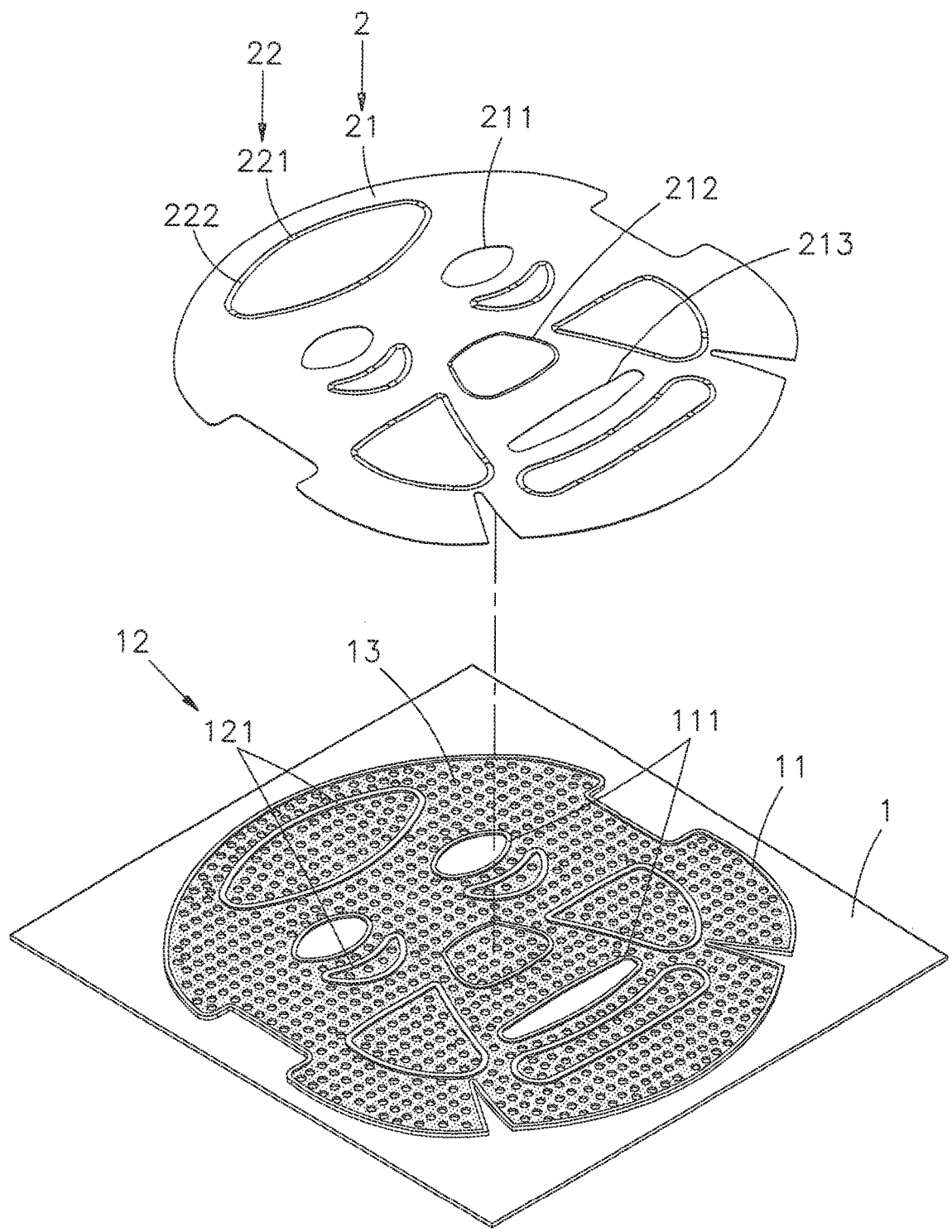
FIG. 2 is an applied view of the present invention.
Figure 3:
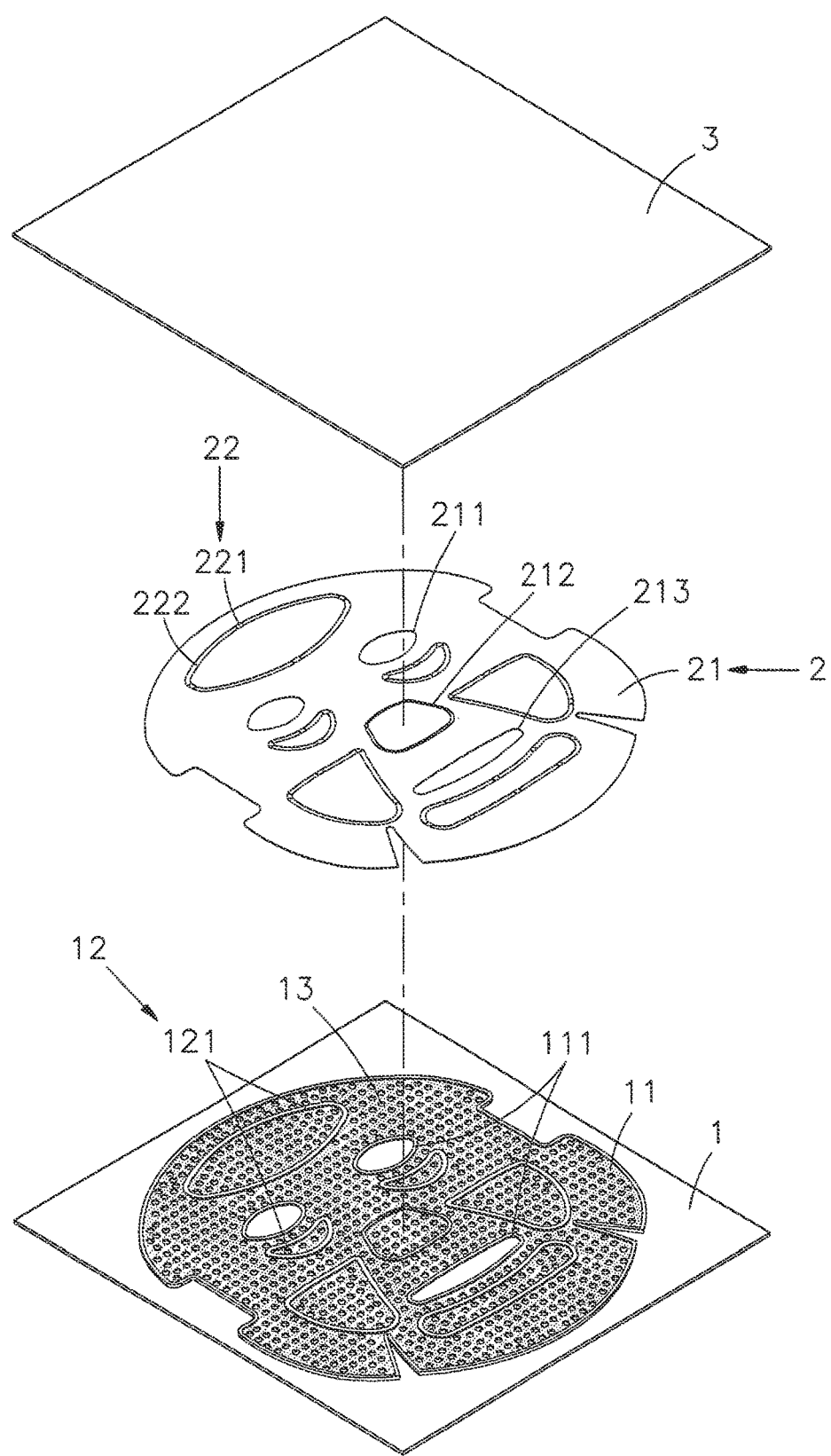
FIG. 3 is another applied view of the present invention.
Figure 4:
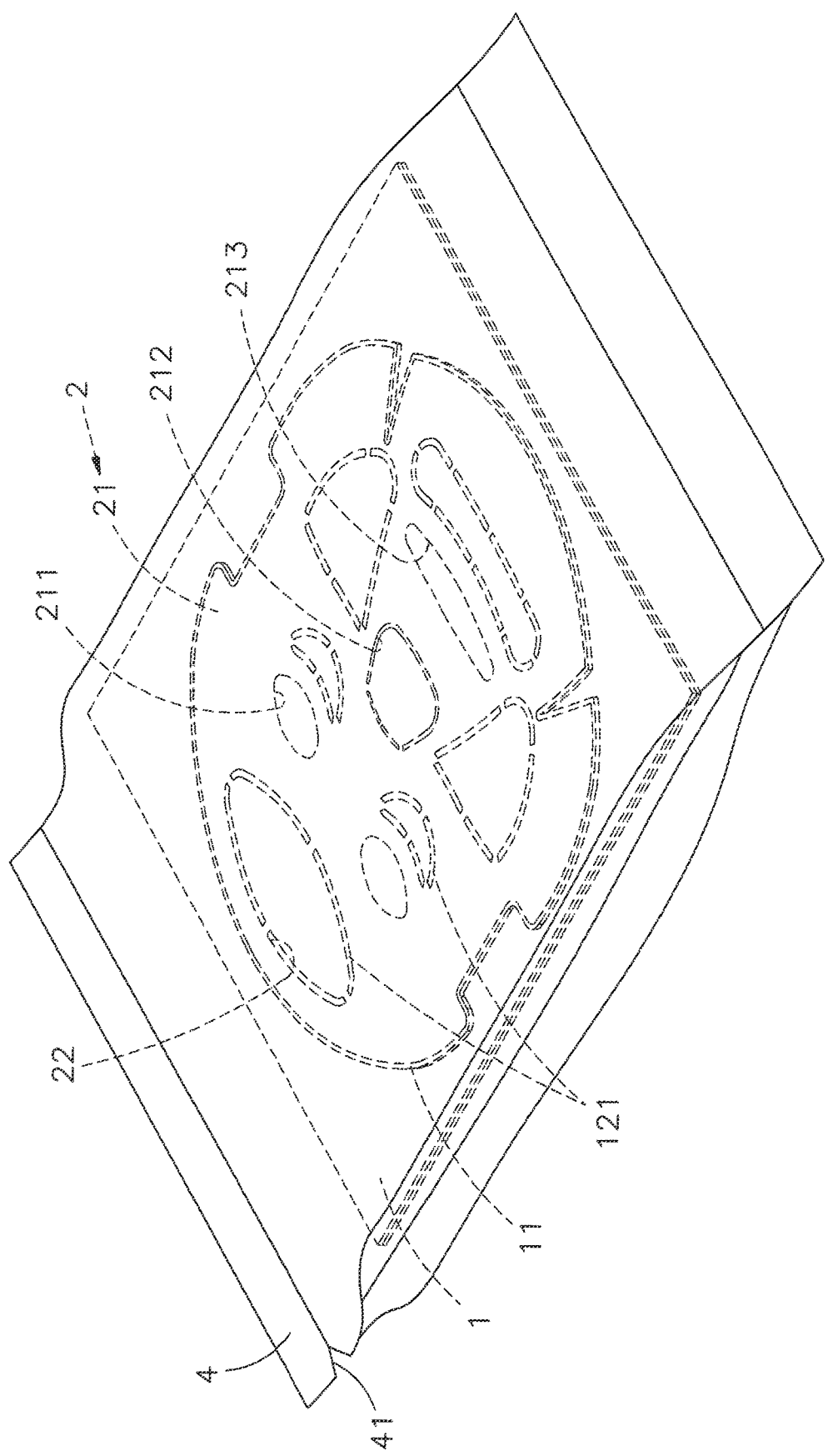
FIG. 4 is yet another applied view of the present invention.

The invention as well as a preferred mode of use, further objectives and advantages thereof will be best understood by reference to the following detailed description of illustrative embodiments when read in conjunction with the accompanying drawings FIGS. 1, 2, 3 and 4 are perspective and applied views of the present invention, respectively. As shown, the disclosed mask tray has a base 1 made of plastic and like a plate in shape. On the base 1, there is an accommodating socket 11 shaped according to a facial mask 2. The accommodating socket 11 is provided with retaining portions 111 at sites positionally corresponding to an average user's eyes and mouth. In addition, the accommodating socket 11 has therein at least one compartment 12, and plural cavities 13 are formed at bottoms of the accommodating socket 11 and of the compartments 12.

The at least one compartment 12 of the base 1 may be located according to an average user's facial skin conditions. For example, people tend to secrete sebum at the forehead, so the base 1 may have a compartment 12 formed above the two retaining portions 111 of the base 1 for two eyes so that the compartment 12 is positionally corresponding to an average user's forehead. Moreover, people tend to have melanin pigmentation and fine wrinkles at eyes' puffs, so the base 1 may also have two compartments 12 below the two retaining portions 111 for two eyes so that the compartments 12 are positionally corresponding to an average user's eye puffs. Additionally, people tend to secrete sebum and in turn have acnes at the nose, so the base 1 may also have a compartment 12 corresponding to the nose. On the other hand, people tend to have the skin at cheeks dehydrated, so the base 1 may also have two compartments 12 at two sides of the nose compartment so that the compartments 12 are positionally corresponding to an average user's cheeks. Furthermore, the chin is another part of the face that tends to be dehydrated, so the base 1 may have a compartment 12 below the retaining portion 111 for the mouth so that the compartment 12 is positionally corresponding to an average user's chin.

The foregoing compartments 12 preferably each have a raised boundary 121 for enclosing an essence suitable for the skin of the corresponding facial part. For example, the compartment 12 for the forehead may be filled with an essence that controls secretion of sebum, and the two compartments 12 corresponding to the eye puffs may be filled with an essence that mitigates melanin pigmentation and fine wrinkles. The raised boundaries 121 thus prevent the essences from flowing out the compartments 12, so that focused skincare treatments can be locally provided to the corresponding parts of facial skin. However, in practical use, the compartments 12 may alternatively be defined by ditches, through holes or other structures that prevent the contained essences from spreading out.

In use, one essence may be filled into the accommodating socket 11 of the base 1, and then one or more other essences may be filled into the at least one compartment 12 according to skincare needs of the corresponding skin part(s). Afterward, a substrate 21 of a facial mask 2 is placed into the accommodating socket 11 so that the substrate 21 of the facial mask 2 absorbs the essence in the accommodating socket 11 and the other essence(s) in the compartment(s) 12 for focused, local skincare. In this way, the facial mask 2 is well equipped for providing local skincare to different parts of the face.

The aforementioned facial mask 2 is preferably a full-face facial mask, with its substrate 21 penetrated to form two eye openings 211, a nose opening 212, and a mouth opening 213, so as to allow an intended user's eyes, nose, and mouth to be exposed at the two eye openings 211, the nose opening 212, and the mouth opening 213. In addition, the facial mask 2 may further contain at least one division 22 that prevents liquid permeation. The at least one division 22 may be positionally corresponding to the at least one compartment 12 of the base 1 so that after different sites of the substrate 21 of the facial mask 2 absorb the essences from the compartments 12 corresponding thereto, the divisions 22 enclose the essences in the sites where different skincare treatments are to be provided.

Additionally, the substrate 21 of the facial mask 2 may be made of non-woven fabric, cotton cloth, silk cloth or bio-fabric, as long as it can absorb liquid. The facial mask 2 may be infused with various liquid skincare ingredients, which allows the facial mask to provide moistening, whitening, sebum control, anti-aging and other skincare treatments. The division 22 may be made of plastic, rubber, or any materials impermeable to liquids or be a separating liquid that separates liquids. Alternatively, the division 22 is provided with a plurality of bridges 221, and a through hole 222 is formed between two adjacent said bridges, or other structures that prevent the liquid in the division 22 from permeating outward.

According to the present invention, before the tray with the mask is packaged, a fixing sheet 3 is attached to the base 1 loaded with the facial mask 2, so that the facial mask 2 is held between the accommodating socket 11 of the base 1 and the fixing sheet 3. Afterward, the assembly is packed in a packing bag 4 for transportation and sale. However, the foregoing packaging is only exemplificative, and many other packing ways may be implemented. For example, the use of the fixing sheet 3 may be omitted, and the base 1 loaded with the facial mask 2 can be directly placed into the packing bag 4, and then air in the packing bag 4 is removed using an external vacuum packing machine (not shown), so that the inside of the packing bag 4 is in vacuum, which forces the packing bag 4 to tightly fit the base 1 and the facial mask 2 from both above and below, thereby holding the facial mask 2 in position in the accommodating socket 11 of the base 1 without shift. The packaging may be implemented differently according to practical applications or needs, and forms no features of the present invention. The simple description provided herein is merely for a reader's easy understanding.

In use, a user can first tear the packing bag 4 from the side notch 41. Then he/she and take the base 1 out of the packing bag 4, remove the facial mask 2 from the accommodating socket 11 of the base 1, and put the facial mask 2 evenly on his/her face. The at least one compartment 12 of the base 1 prevents the essence in the compartment 12 from mixing with the essence filled in the accommodating socket 11, so that the facial mask 2 can absorb different essences and provide focused local skincare treatment specific to different facial parts. For example, the facial mask 2 provides focused skincare treatments specific to a user's forehead, eye puffs, nose, cheeks and chin while providing a general treatment to the user's entire face. In this manner, a single facial mask can provide local care to every site of the face respectively, thereby improving the overall skincare effects.

In addition, according to the present invention, the base 1 is provided with a plurality of cavities 13. When different essences are dilled into the accommodating socket 11 of the base 1 and at least one compartment 12, and a substrate 21 of a facial mask 2 is placed in the accommodating socket 11, minute gaps exist between the base 1 and the facial mask 2 due to spaces defined by the cavities 13. Capillarity thus exists between these gaps 13 and the essences and holds the essences in the cavities 13, thereby preventing the essences from spilling out the base 1 during transportation while providing users with improved skincare effects.

Thus, the present invention features that the base 1 has the accommodating socket 11 that includes at least one compartment 12, and the compartments 12 may be filled with different essences according to skincare needs of different facial skin parts. When the accommodating socket 11 is loaded with a facial mask 2, the facial mask 2 locally absorbs the different essences in the compartments 12, thereby enabling the facial mask 2 when put on a user's face to provide local skincare treatments catering for different facial skin parts, thereby improving the overall skincare effects. Therefore, all structures and devices providing equivalent effects should be deemed covered by the scope of the present invention, and should be encompassed by the appended claims.

What is claimed is:

1. A facial mask tray, comprising a base on which an accommodating socket is formed for fittingly receiving a facial mask therein, the accommodating socket including:
a plurality of compartments that prevent diffusion between a plurality of predetermined essences; and
a plurality of retaining portions positionally corresponding to two eyes and a mouth of an average human face;
wherein a first compartment of the plurality of compartments is disposed above the retaining portions for the two eyes, and a pair of second compartments of the plurality of compartments are disposed below respective retaining portions for the two eyes, a third compartment of the plurality of compartments is disposed below the retaining portion for the mouth, a fourth compartment of the plurality of compartments is positioned to correspond to a nose of the average human face, and a pair of fifth compartments of the plurality of compartments are respectively positioned in spaced relationship at two sides of the fourth compartment.

2. The facial mask tray of claim 1, wherein the base is a plate made of a plastic material.

3. The facial mask tray of claim 1, wherein cavities are formed at a bottom of the accommodating socket of the base and at respective bottoms of the plurality of compartments.

4. A facial mask package, comprising a tray, a facial mask, and a fixing sheet, wherein:
the tray has an accommodating socket that is shaped according to the facial mask and has at least one compartment for preventing a plurality of predetermined essences from mutual diffusion;

the facial mask has a substrate to be received in the accommodating socket and at least one division corresponding to the at least one compartment for preventing the plurality of predetermined essences from permeation; and the fixing sheet is deposited over the facial mask and combined with the tray.

5. The facial mask package of claim 4, wherein the at least one division of the facial mask has a plurality of bridges, and a through hole formed between two adjacent of said bridges for preventing a predetermined essence of the plurality of predetermined essences from permeation.

* * * * *